(12) United States Patent
Herresthal

(10) Patent No.: US 8,845,567 B2
(45) Date of Patent: Sep. 30, 2014

(54) KNEE BANDAGE

(75) Inventor: Jens Herresthal, Frankfurt (DE)

(73) Assignee: Medi GmbH & Co. KG, Bayreuth (DE)

( * ) Notice: Subject to any disclaimer, the term of this patent is extended or adjusted under 35 U.S.C. 154(b) by 466 days.

(21) Appl. No.: 13/000,735

(22) PCT Filed: Jun. 24, 2009

(86) PCT No.: PCT/EP2009/004565
§ 371 (c)(1),
(2), (4) Date: Mar. 16, 2011

(87) PCT Pub. No.: WO2009/156143
PCT Pub. Date: Dec. 30, 2009

(65) Prior Publication Data
US 2011/0160631 A1    Jun. 30, 2011

(30) Foreign Application Priority Data

Jun. 25, 2008 (DE) .......................... 10 2008 029 825

(51) Int. Cl.
| | | |
|---|---|---|
| *A61F 13/00* | (2006.01) | |
| *A61F 13/06* | (2006.01) | |
| *A61F 5/01* | (2006.01) | |
| *A61F 5/30* | (2006.01) | |

(52) U.S. Cl.
CPC ............. *A61F 13/062* (2013.01); *A61F 5/0109* (2013.01); *A61F 2005/0176* (2013.01); *A61F 5/30* (2013.01)
USPC .................................. 602/26; 602/62; 602/63

(58) Field of Classification Search
CPC ... A61F 5/0585; A61F 5/0118; A61F 5/0111; A61F 5/0123; A61F 13/00; A61F 13/14; A61F 13/061; A61F 13/08

USPC ......... 602/5, 23, 26, 60–64; 2/455, 62, 22–26
See application file for complete search history.

(56) References Cited

U.S. PATENT DOCUMENTS

| | | | |
|---|---|---|---|
| 3,934,583 A | | 1/1976 | Hollingshead et al. |
| 3,945,046 A | | 3/1976 | Stromgren |
| 4,425,912 A | * | 1/1984 | Harper ............................. 602/26 |
| 4,445,505 A | * | 5/1984 | Labour et al. ................... 602/26 |
| 5,016,621 A | * | 5/1991 | Bender ............................ 602/26 |
| 6,287,269 B1 | | 9/2001 | Osti et al. |
| 7,173,161 B1 | * | 2/2007 | Kandt .............................. 602/41 |
| 2005/0020951 A1 | * | 1/2005 | Gaylord et al. ................. 602/26 |
| 2005/0283106 A1 | | 12/2005 | Smith et al. |
| 2007/0167891 A1 | | 7/2007 | Gramza et al. |
| 2009/0013442 A1 | * | 1/2009 | Matuszak et al. .................... 2/23 |
| 2009/0163840 A1 | * | 6/2009 | Chiang .............................. 602/5 |
| 2010/0036303 A1 | * | 2/2010 | Bauerfeind et al. ............ 602/26 |

FOREIGN PATENT DOCUMENTS

| | | | |
|---|---|---|---|
| CN | 20123918 Y | * | 5/2009 |
| DE | 8115670 A | | 8/1981 |
| DE | 36 37 879 A1 | | 5/1988 |
| DE | 3838576 | | 5/1991 |
| DE | 298 03 103 U1 | | 5/1998 |

(Continued)

*Primary Examiner* — Kim M Lewis
(74) *Attorney, Agent, or Firm* — Lucas & Mercanti, LLP

(57) ABSTRACT

A knee bandage is provided comprising a bandage base element and at least one massage pelotte. The bandage base element includes a central kneecap region, a thigh region and a lower leg region. The massage pelotte is fixed in the massage region of the base element and has massage elements oriented inwards towards the leg. The massage region is located in the thigh region and is allocated to a trigger point or trigger region of the musculus vastus lateralis.

13 Claims, 3 Drawing Sheets

(56) References Cited

FOREIGN PATENT DOCUMENTS

| | | |
|---|---|---|
| DE | 202004001936 | 7/2004 |
| EP | 1093779 | 4/2001 |
| EP | 1093779 A2 | 4/2001 |
| JP | 3020250 U | 1/1996 |
| JP | 9220271 A | 8/1997 |
| JP | 2000037409 A | 2/2000 |
| JP | 3037352 U | 3/2000 |

* cited by examiner

KNEE BANDAGE

The present application is a 371 of International application PCT/EP2009/004565 filed Jun. 24, 2009, which claims priority of DE 10 2008 029 825.5, filed Jun. 25, 2008, the priority of these applications is hereby claimed and these applications are incorporated herein by reference.

The invention relates to a knee bandage.

BACKGROUND OF THE INVENTION

Knee bandages (or knee joint bandages) are known in a variety of embodiments. In particular embodiments, knee bandages have a function of mechanical correction of dislocations of the kneecap (patella). In this case, by mechanical aids such as straps, a lateral pressure may be exerted externally on the patella in order to counteract the dislocation of the patella. Knee joint bandages of this type are known for example from DE 10 2004 04 793 A1 or DE 38 38 576 A1 or from U.S. Pat. No. 6,287,269 B1.

The anatomical guidance of the patella is effected on the one hand passively by the trochlea, and on the other it is heavily dependent in movement on the dynamics of the various muscular forces of the lateral wide thigh muscle (musculus vastus lateralis) and of the wide thigh muscle oriented towards the centre (musculus vastus medialis). Centrally and laterally to the kneecap and the kneecap ligament extends a ligament, the retinaculum patellae, which is divided into a central portion, the retinaculum patellae mediale, which arises from the musculus vastus medialis, and a lateral portion, the retinaculum patellae laterale, which is formed from the musculus vastus lateralis or to which are attached a few muscle fibres of the musculus vastus lateralis, and which is connected on the other side to the lateral edge (margo lateralis) of the patella as an attachment face. The lower region of the musculus vastus lateralis is attached at the distal end to the femur (thigh bone) and to the lateral edge of the patella and pulls by means of the Lig. patellae over the knee. Whilst the musculus vastus lateralis pulls the patella laterally or outwards, the musculus vastus medialis pulls the patella inwards or medially. In the entire possible scope of movement of the knee, the patellofemural system, i.e. the system linking the patella to the femur, must remain in equilibrium by a balanced muscular interplay. An isolated contraction of the musculus vastus lateralis produces a subluxation of the patella in the lateral direction, for example.

If the patellofemural system gets out of equilibrium due to a muscular imbalance, then in particular an abnormal patella tilt arises, which unlike luxation causes an increased load on the lateral facet of the lateral patella. An adapted contraction of the lateral retinaculum or a faulty load on the retinaculum thus leads to an increased risk of retropatellar cartilage defect. Such permanent faulty loads may thus lead to more rapid wear of the cartilage and may for example be provoked by a relatively long resting of the muscle in the contracted position, e.g. fully extended knee in sitting or lying position.

The load from contracted muscles additionally leads to the formation of muscular trigger points which produce local and referred pain. The trigger points in the distal musculus vastus lateralis, which may lead to blockage of the patella, usually lie at the surface. These are best located with the knee extended.

Ischaemic compression (e.g. tennis ball method) is known, which effects deactivation of most superficial trigger points of the musculus vastus lateralis.

SUMMARY OF THE INVENTION

The object of the invention is to indicate a new knee bandage.

This is achieved according to the invention with the features as described herein. Developments and embodiments of the knee bandage according to the invention will be described herein.

The invention is based on the knowledge of providing a targeted massaging effect of a massage pelotte (or friction pelotte) provided on the knee bandage on to a trigger region or trigger point of the musculus vastus lateralis. Unexpectedly, it was found that this enabled functional defects or imbalances such as for example tensing or contraction of the musculus vastus lateralis to be alleviated or positively influenced. The massage pelotte on the knee bandage reduces the tone of the musculus vastus lateralis, whereby an imbalance of the musculus vastus medialis due to muscular imbalance can be intentionally corrected and the entire guidance of the patellofemural system can be optimised. In particular, the knee bandage according to the invention can help to prevent the possible start of retropatellar arthritis, by reducing the abnormal patella tilt and hence the retropallelar pressure, or also help to counteract luxation or lateralisation of the patella. This new mode of operation of the knee bandage synergistically combines knee-joint statics with muscle function.

The knee bandage according to the invention therefore comprises in at least one trigger region or trigger point of the musculus vastus lateralis relative to the kneecap, at least one massage pelotte, which acts by means of massage elements or massage points or massage surfaces on such massage elements oriented inwards on the leg, particularly when the knee is in movement, continuously on this trigger region or point on the musculus vastus lateralis by the exertion of a massage pressure and/or massage friction, and thus counteracts the unwanted transverse forces acting laterally outward on the kneecap by the musculus vastus lateralis, or reduces these transverse forces.

Preferably, the massage region in which the massage pelotte is disposed is allocated to the trigger region or trigger point in the distal edge region or transitional region of the musculus vastus lateralis, which extends to or into the retinaculum laterale. This trigger point is also termed the trigger point 1 of the musculus vastus lateralis.

The massage pressure of the massage pelotte is adjusted to achieve the desired effect in a defined manner. In order to be able to adjust the massage pressure by the massage pelotte to suit the patient and the diagnosis, in an advantageous embodiment at least one tension element is provided for adjusting the pressure of the massage pelotte inward on to the trigger point.

The tension element comprises in particular a tension belt, which is adjustable in length and/or can extend diagonally over the thigh region.

Alternatively or in addition, the tension element may also comprise an in particular elastical intermediate element, which is clamped to the massage pelotte or disposed between a tension belt or an elastical region of the bandage base element and the massage region and thus exerts an additional pressure on the massage region. The application pressure and also its elasticity is then adjustable via the thickness of the intermediate element. The tension belt can thus be formed as a simple belt without length adjustment, in particular as a Velcro® or similar type of strip.

The massage effect is further adjusted or influenced by the shape and the material of the massage pelotte.

Thus the massage pelotte may have a base body, and the massage elements may be formed in particular in one piece or in a common shaped body on the base body, in particular in the shape of preferably half-shell or semi-spherical or ridged or wave-shaped bumps. The massage elements may preferably have dimensions perpendicular to or in the direction away from the base body in a range of between 1 mm and 8 mm. The basic configuration of the base body may in particular be rectangular or triangular or trapezoid or oval.

A preferred material for the massage pelotte or (at least) the massage elements is an elastomer, in particular with a silicone base or polysiloxane base, wherein the elastomer preferably has a Shore A hardness of between 20 and 80 Shore A, in particular between 55 and 65 Shore A.

Advantageously, the massage pelotte is disposed in a pocket, for example sewn or glued on, on the inner face of the bandage base element on the side associated with the leg.

Furthermore, in a further embodiment, at least one correction element for mechanical correction of the patella luxation can be provided, in particular a correction belt disposed on the exterior of the patella.

In a further embodiment, the tension element or tension belt may be at least partially incorporated or formed in one piece with the correction element or correction belt or fixed or connected thereto.

BRIEF DESCRIPTION OF THE DRAWING:

The invention is explained more fully below with the aid of embodiments and with reference to the drawings, which show.

Figure 1:
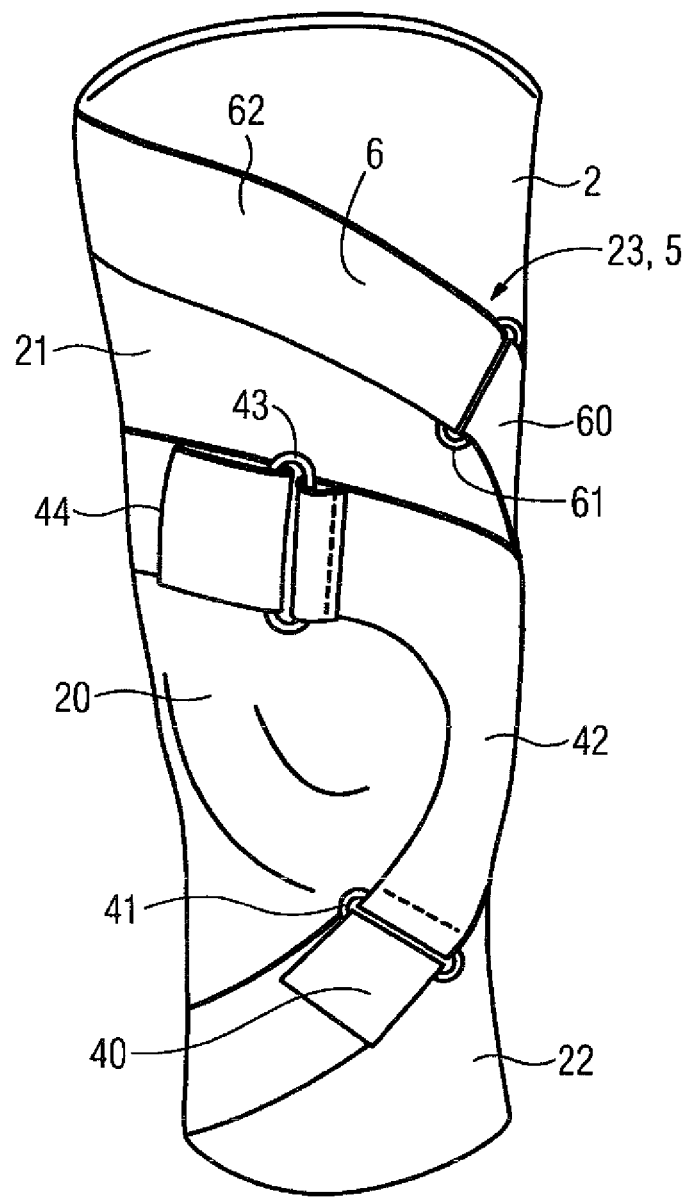
FIG. 1 a knee bandage according to the invention in a front perspective view.
Figure 2:
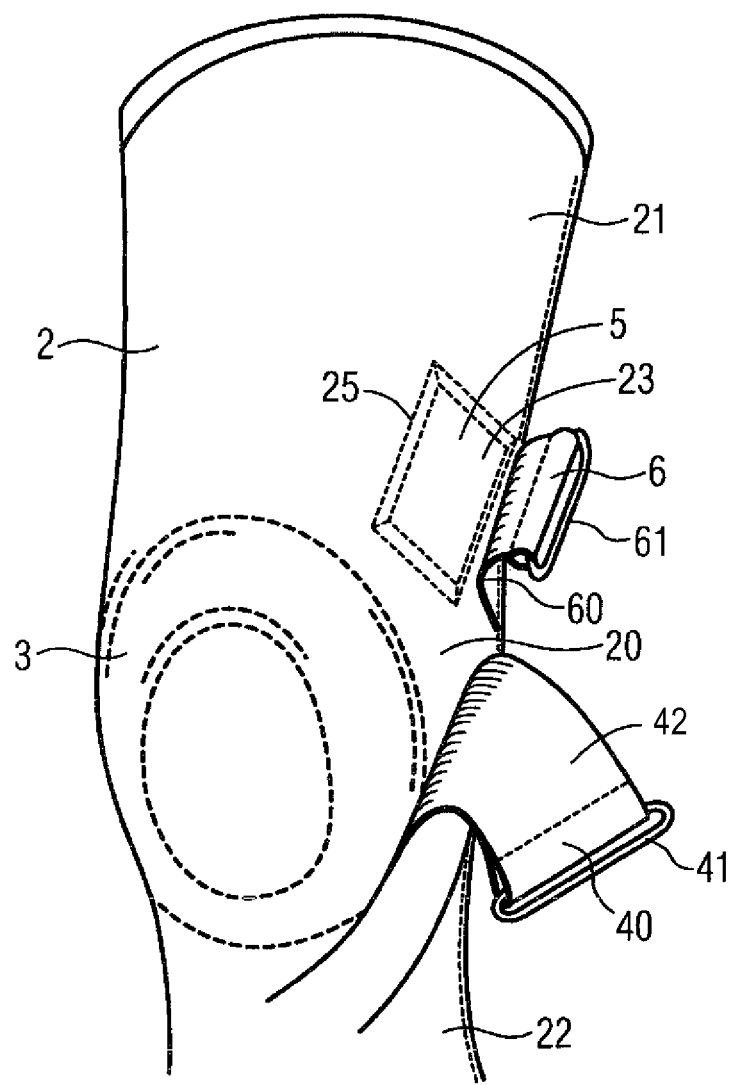
FIG. 2 the knee bandage according to FIG. 1 with detached and partly not shown tension belts and a massage pelotte located on the inner face in a perspective view and FIG. 3 a massage pelotte for a knee bandage according to FIG. 1 and FIG. 2 in a perspective view FIG. 4 a further embodiment of a knee bandage according to the invention in a perspective view and each drawing is shown schematically. Corresponding parts and dimensions are provided with the same reference numbers in FIGS. 1 to 4.

DETAILED DESCRIPTION OF THE INVENTION:

The knee bandage according to FIGS. 1 and 2 comprises an in particular hose-like or tubular bandage base element 2, which generally consists of an elastical material, in particular a textile, a fabric or a hosiery material. Suitable materials are, without limitation in general, textile materials with a base of manmade fibres or also cotton.

The bandage base element 2 when put on fully encompasses the affected knee and an adjoining portion of the lower leg and thigh. The central kneecap region comprising the knee joint itself, the knee hollow and the kneecap is referenced 20, the thigh region adjoining the thigh is referenced 21, and the lower leg region adjoining the lower leg is referenced 22.

In the kneecap region 20, an annular edge element (or annular pelotte) 3 is fixed to the bandage base element 2 and encloses the kneecap or patella not shown and consists in particular of an elastical and/or damping material, e.g. a silicone elastomer (elastomer and polysiloxane base) or another elastomer. The edge element 3 is fixed to the inner face of the bandage base element 2 associated with the knee or leg directly by adhesion or indirectly by insertion into a corresponding pocket.

On the exterior of the bandage base element 2, the edge element 3 is surrounded by a half-moon or approximately semi-circular or semi-oval correction strap (or: correction belt) 42, which in its central region is fixed to the exterior of the bandage base element 2, in particular by gluing or sewing. The correction strap 42 may be tensioned inwards or medially at its free ends via a respective one of two eyes (or: elongate rings) 41 and 43 respectively to a first tension belt 40, which extends below the edge element 3 and is fixed in the lower leg region 22 of the bandage base element 2, and to a second tension belt 44, which extends above the edge element 3 and is fixed in particular in the transitional region between the kneecap region 20 and the thigh region 21 of the bandage base element 2. The two tension belts 40 and 44 can to this end be tensioned via Velcro® or similar type of elements not shown to various lengths and therefore to different tightnesses, so that the correction force acting by the correction strap 42 on the kneecap medially inwards from the exterior can be adjusted to the kneecap for mechanical correction of a luxation.

Above the correction strap 42, on the bandage base element 2, a massage pelotte 5 is fixed to the bandage base element 2 on the inner face of the bandage base element 2 associated with the leg, in particular is disposed in a pocket 25 on the inner face. The pocket 25 is closed all round and may in particular be formed by a piece of textile material glued or sewn to the inner face of the bandage base element 2.

Figure 3:
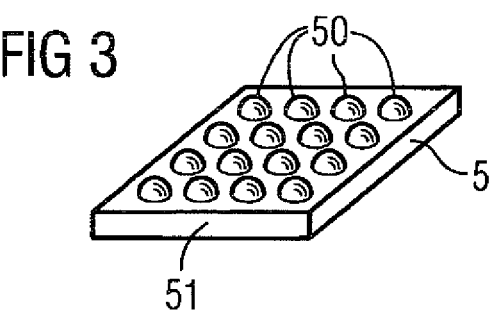

The massage pelotte 5 can, as is shown in FIG. 3, have individual massage elements 50 on one base body 51, which in particular have local massage areas or massage points, in particular by forming as half-shells or semi-spherical elements. Likewise, however, in an embodiment not shown, massage elements with linear massage areas may be provided on the massage pelotte in particular in the form of ridges or waves. The massage elements 50 extend from the inner face of the bandage base element 2 away up to the leg and act through the material of the pocket 25 in a massaging manner on the area of the patient's leg lying below the massage region 23 of the bandage base element 2. The massage pelotte 5 preferably consists also of a silicone elastomer (elastomer with a polysiloxane base) or another elastomer. The massage pelotte 5 preferably has an elasticity suitable for the desired massaging effect, preferably a Shore A hardness of the massage pelotte 5 of between 20 and 80 Shore A, in particular between 55 and 65 Shore A being selected.

The base body 51 of the massage pelotte 5 in the embodiment of FIG. 3 has an elongate rectangular base shape and has a substantially constant thickness, at least outside the regions with the massage elements 50.

The massage pelotte 5 or its base body 51 may however also have a different shape, e.g. an oval, polygonal, in particular triangular or trapezoid, base shape and additionally or alternatively also extend slightly curved so as to adapt to the knee and leg shape at the site of the massage region 23. The base area of the base body 51 is adapted to the size of the massage region 23. The shape, length and thickness of the massage elements 50 and the surface density of their arrangement on the base body 51 and the thickness of the base body 51 itself are adapted to the desired massaging effect. Typical values for the thickness of the base body 51 are 2 mm to 8 mm and for the length of the massage elements 50, measured outwards from the base body 51, 1 mm to 8 mm.

The massage region 23 of the knee bandage or its bandage base element 2 is so arranged that when the knee bandage is put on it comes to rest directly at a trigger point or trigger region of the musculus vastus lateralis relative to the patella, preferably on or over the trigger point 1 of the musculus vastus lateralis, i.e. viewed anatomically at the distal edge region or transitional region of the musculus vastus lateralis extending into the retinaculum patellae laterale.

Thus the massage pelotte 5 disposed in the massage region 23 can act in a massaging manner on the trigger point or region of the musculus vastus lateralis lying below, on the one hand perpendicularly inwards, on the other hand also by the movement laterally or along the surface. This produces a massaging effect by the massage pelotte 5 of the knee bandage, whereby tightening and contracting of the trigger region or point of the musculus vastus lateralis relative to the patella are alleviated and hence a force exerted outward or laterally by the vastus lateralis on the kneecap is counteracted. In particular, this reduces abnormal, pathological tilt of the patella.

On or in the massage region 23, a tension belt 6 is provided, which extends obliquely over the thigh region 21 of the bandage base element 2 up to the kneecap region 20 or transitional region with the kneecap region 20 and has two tension belt parts 60 and 62 which are fixed, in particular glued or sewn, respectively to the mutually remote end regions of the bandage base element 2 on its outer face remote from the leg, and are connected or connectable together at the mutually associated regions or ends via an eye (or: an elongate annular element) 61. In this case, Velcro® or similar type of elements are provided on the longer tension belt part 62, via which the length of the said tension belt part 62 can be adjusted and hence the tensile force or tension of the entire tension belt 6 can be adjusted by varying the length of the tension belt. The tension belt 6 thus acts with varying adjustable pressure on the massage region 23 located under the tension belt 6, in particular under the first tension belt part 60 and the eye 61 and the massage pelotte 5 located there, depending on the length set of the second tension belt part 62. Thus by varying the tension pressure by means of the tension belt 6, the massage pressure acting through the massage elements 50 on the massage pelotte 5 inward on the trigger point of the musculus vastus lateralis can be adjusted in a controlled manner according to the patient and diagnosis.

The shorter tension belt part 60 is preferably permanently connected to the eye 61 and is not adjustable in length. The longer tension belt part 62 is adjustable via Velcro® or similar type of fastenings or elements and extends transversely over the entire thigh region 21 to the opposite (medial) side, whilst the shorter tension belt element 60 is disposed at the distal side of the bandage base element 2, in its thigh region 21. By the diagonal arrangement of the tension belt 6, a wide length adjustment range is achieved and hence a good, variable tension effect and exertion of the massaging pressure.

Figure 4:
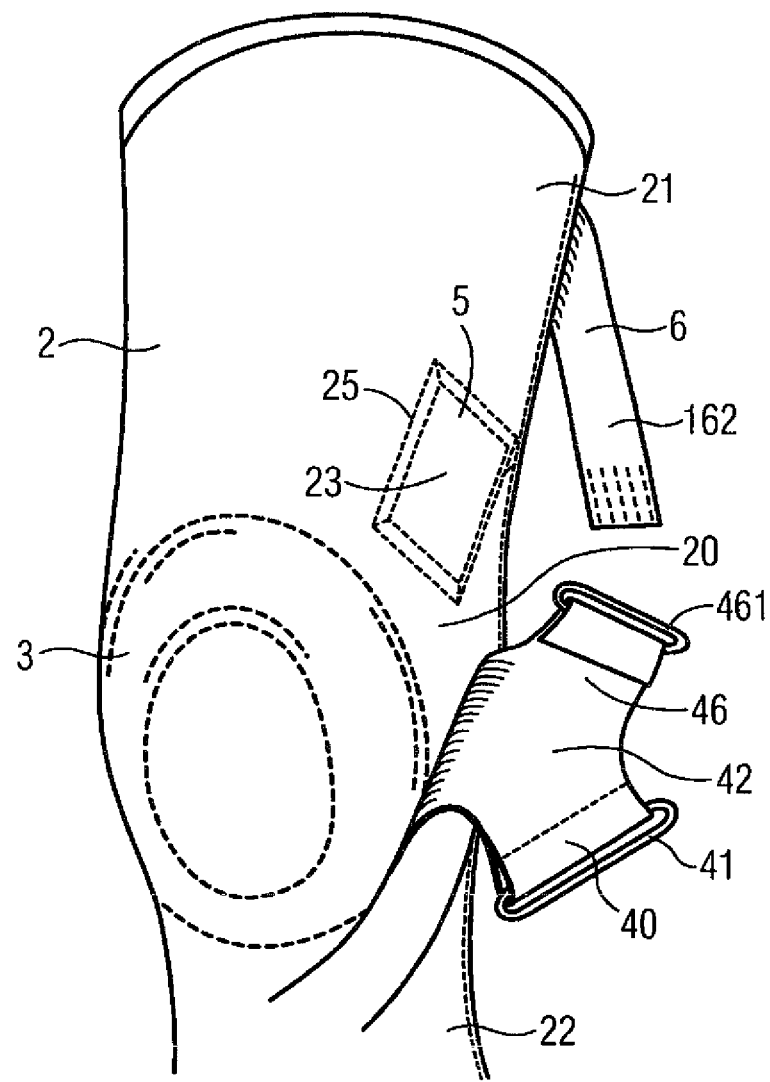

In the embodiment according to FIG. 4, on the correction strap or correction belt 42 for the edge element 3 of the kneecap, a part 46 of the tension belt 6 is formed for the massage region 23 and the massage pelotte 5. The correction strap 42 is to this end formed approximately T-shaped with a belt 40 and an eye 41 similarly to FIG. 2 and additionally with a tension belt part 46 with an eye 461, to which a second tension belt part 162 of the tension belt 6 may be fixed. The tension belt 6 assembled from the two tension belt parts 46 and 162 in the fixed state then extends transversely or diagonally from outside or distally in the medial direction towards the kneecap or the edge element 3 via the massage region, and again the tension or application pressure of the massage pelotte 5 can be adjusted by Velcro® or similar type of elements on the tension belt part 162.

In this embodiment, therefore, the tension belt is partly incorporated or formed in one piece with the correction belt. In a modification, the correction belt 42 could also be welded or sewn to the bandage base element 2 and also the tension belt 6 could be fixed to this welded or sewn seam. Finally, the tension belt and correction belt could also be punched from one component and fixed to the outer upper edge.

LIST OF REFERENCE NUMBERS 2 bandage base element
3 edge element
5 massage pelotte
6 tension belt
20 kneecap region
21 thigh region
22 lower leg region
23 massage region
25 pocket
41 eye
42 correction strap
43 eye
44 tension belt
46 tension belt part
50 massage element
51 base body
60 tension belt part
61 eye
62 tension belt part
162 tension belt part
461 eye

The invention claimed is:

1. A knee bandage, comprising:
a) an elastic, tubular bandage base element designed to fit over a knee of a leg, the bandage base element having a central kneecap region designed to fit a kneecap, a thigh region at one end of the base element, adjoining the kneecap region and designed to fit a partial region of a thigh and a lower leg region at an other end of the base element adjoining the kneecap region and designed to fit a partial region of a lower leg;
b) at least one massage pelotte, which is fixed in a massage region of the bandage base element and has massage elements oriented inwards towards the leg when the knee bandage is on;
c) the massage region with the at least one massage pelotte is disposed in the thigh region and is designed to fit a trigger point or trigger region of the musculus vastus lateralis or where n the massage pelotte effects massage of a trigger point or trigger region of the musculus vastus lateralis when the knee bandage is put on, and the knee is moved; and
d) at least one length adjustable tensioning belt fixed on an outer face of the bandage base element, the at least one length adjustable tensioning belt extending obliquely with respect to the bandage base element, from the thigh region to a transitional region between the kneecap region and the thigh region of the bandage base element, the tensioning belt extending over the at least one massage pelotte such that the inward pressure of the at least one massage pelotte is adjustable by adjusting the length of the tensioning belt.

2. The knee bandage according to claim 1, in which the massage pelotte has a base body and the massage elements are formed or provided on the base body in the form of bumps.

3. The knee bandage according to claim 2, in which at least some of the massage elements are formed or provided on the base body in the form of half-shell-shaped or semi-spherical bumps.

4. The knee bandage according to claim 2, in which at least some of the massage elements are formed or provided on the base body in the form of ridge-shaped or wave-shaped bumps.

5. The knee bandage according to claim 2, in which the massage elements have dimensions perpendicular to or in a direction away from the base body of in a range between 1 mm and 8 mm.

6. The knee bandage according to claim 1, in which the massage pelotte or the massage elements are formed from an elastomer with a silicone base or polysiloxane base, and has a Shore A hardness of between 20 and 80 Shore A.

7. The knee bandage according to claim 1, in which the massage pelotte is disposed in a pocket on an inner face of the bandage base element.

8. The knee bandage according to claim 1, having at least one correction element which is disposed on the bandage base element at a lateral side of the kneecap in order to exert a lateral force medially inwards on the kneecap.

9. The knee bandage according to claim 1, in which the tensioning belt has two tension belt parts, which are fixed to mutually remote end regions of the bandage base element respectively, and are connected together via a connecting element.

10. The knee bandage according to claim 9, in which fastening elements are provided on one of the tension belt parts, via which the length of this tension belt part can be adjusted.

11. The knee bandage according to claim 1, in which the at least one tensioning belt comprises at least elastical intermediate element which is clamped or clampable or disposed or disposable between the tensioning belt and the massage region with the massage pelotte and exerts a pressure on the massage region.

12. The knee bandage according to claim 11, in which an application pressure is adjustable via a thickness of the intermediate element.

13. The knee bandage according to claim 1, in which the massage region with the massage pelotte is allocated to the trigger point or region in a distal edge region or transition region of the musculus vastus lateralis, which extends to the or into the retinaculum patellae laterale.

* * * * *